(12) United States Patent
Scurtescu et al.

(10) Patent No.: US 11,793,604 B2
(45) Date of Patent: Oct. 24, 2023

(54) ULTRASONIC METHODS AND DEVICES FOR ORTHODONTIC TREATMENT WITH ALIGNERS

(71) Applicant: SMILESONICA INC., Edmonton (CA)

(72) Inventors: Cristian Scurtescu, Edmonton (CA); Michael Cook, Edmonton (CA)

(73) Assignee: Smilesonica INC., Edmonton (CA)

( * ) Notice: Subject to any disclaimer, the term of this patent is extended or adjusted under 35 U.S.C. 154(b) by 89 days.

(21) Appl. No.: 16/477,775

(22) PCT Filed: Jan. 18, 2018

(86) PCT No.: PCT/CA2018/050056
§ 371 (c)(1),
(2) Date: Jul. 12, 2019

(87) PCT Pub. No.: WO2018/132912
PCT Pub. Date: Jul. 26, 2018

(65) Prior Publication Data
US 2020/0121420 A1 Apr. 23, 2020

Related U.S. Application Data

(60) Provisional application No. 62/447,833, filed on Jan. 18, 2017.

(51) Int. Cl.
*A61C 7/00* (2006.01)
*A61C 7/08* (2006.01)
(Continued)

(52) U.S. Cl.
CPC .............. *A61C 7/002* (2013.01); *A61C 7/008* (2013.01); *A61C 7/08* (2013.01); *A61C 19/06* (2013.01); *G16H 10/65* (2018.01)

(58) Field of Classification Search
CPC .......... A61C 7/002; A61C 7/08; A61C 7/008; A61C 7/00; A61C 19/06; A61C 2204/005;
(Continued)

(56) References Cited

U.S. PATENT DOCUMENTS 9,232,986 B2 * 1/2016 Scurtescu ................ A61C 7/00
9,730,780 B2 * 8/2017 Brawn .................... A61C 19/06
(Continued)

FOREIGN PATENT DOCUMENTS

WO 2011134071 11/2011
WO 2011134071 A1 11/2011
(Continued)

OTHER PUBLICATIONS

Aug. 27, 2020 EPO Search Report.

*Primary Examiner* — Edward Moran
*Assistant Examiner* — Matthew P Saunders
(74) *Attorney, Agent, or Firm* — Russell Manning; FisherBroyles LLP

(57) ABSTRACT

Ultrasonic devices, systems, and methods for orthodontic treatment performed with aligners are described. Such devices, systems, and methods are to provide multiplicative treatment duration shortening for patients under orthodontic treatment with aligners, such as clear aligners. Communication of desired ultrasound treatment can be communicated from an aligner to an ultrasound device by a communication module using an identification number on the aligner and entering the identification number into the system, an identification number on an external document and entering the identification number into the system, a scannable code and code reader, and an assessment by a dentist and entering the assessment into the system, a radio-frequency identification (RFID) transponder and RFID reader, a change in material
(Continued)

properties of the aligner and reading the material properties, or a change in optical properties and reading the optical properties.

19 Claims, 18 Drawing Sheets

(51) Int. Cl.
    *A61C 19/06* (2006.01)
    *G16H 10/65* (2018.01)

(58) Field of Classification Search
    CPC ... A61N 7/00; A61N 2007/0078; G16H 10/65
    USPC .......................................................... 433/6
    See application file for complete search history.

(56) References Cited

U.S. PATENT DOCUMENTS

| | | | | |
|---|---|---|---|---|
| 9,775,687 | B1* | 10/2017 | Hoyberg | A61C 7/006 |
| 9,907,626 | B1* | 3/2018 | Lowe | A61C 7/008 |
| 10,092,374 | B2* | 10/2018 | Yamamoto | A61C 7/008 |
| 2002/0129454 | A1* | 9/2002 | Hilscher | A61C 17/222 |
| | | | | 15/22.1 |
| 2004/0013993 | A1* | 1/2004 | Ito | A61C 7/008 |
| | | | | 433/6 |
| 2009/0042159 | A1* | 2/2009 | Yamamoto | A61C 7/008 |
| | | | | 433/18 |
| 2009/0061375 | A1* | 3/2009 | Yamamoto | A61C 7/006 |
| | | | | 433/6 |
| 2009/0061379 | A1* | 3/2009 | Yamamoto | A61C 7/08 |
| | | | | 433/24 |
| 2009/0149722 | A1* | 6/2009 | Abolfathi | A61B 5/682 |
| | | | | 600/301 |
| 2012/0094246 | A1* | 4/2012 | Pavlin | A61C 7/08 |
| | | | | 433/6 |
| 2012/0322018 | A1* | 12/2012 | Lowe | A61C 7/00 |
| | | | | 433/24 |
| 2013/0040264 | A1* | 2/2013 | Scurtescu | A61C 7/00 |
| | | | | 433/119 |
| 2013/0280671 | A1* | 10/2013 | Brawn | A61N 5/0603 |
| | | | | 433/24 |
| 2014/0023983 | A1* | 1/2014 | Lowe | A61C 7/08 |
| | | | | 433/24 |
| 2014/0072932 | A1* | 3/2014 | Brawn | A61C 19/06 |
| | | | | 433/173 |
| 2014/0335467 | A1* | 11/2014 | Yamamoto | A61C 7/008 |
| | | | | 433/6 |
| 2015/0130885 | A1 | 5/2015 | Meguro et al. | |
| 2015/0140502 | A1* | 5/2015 | Brawn | A61C 19/06 |
| | | | | 433/24 |
| 2015/0173856 | A1* | 6/2015 | Lowe | A61C 7/00 |
| | | | | 433/24 |
| 2015/0313572 | A1* | 11/2015 | Gerbaulet | A61B 8/4494 |
| | | | | 433/29 |
| 2016/0120615 | A1* | 5/2016 | Scurtescu | A61C 1/0007 |
| | | | | 433/27 |
| 2016/0184054 | A1* | 6/2016 | Lowe | A61C 7/00 |
| | | | | 433/24 |
| 2017/0080249 | A1* | 3/2017 | Brawn | A61N 5/103 |
| 2019/0029522 | A1* | 1/2019 | Sato | A61C 9/0053 |
| 2019/0083202 | A1* | 3/2019 | Brawn | A61C 7/08 |

FOREIGN PATENT DOCUMENTS

| | | | |
|---|---|---|---|
| WO | WO-2011134071 A1 * | 11/2011 | ............ A61C 7/00 |
| WO | 2015058284 | 4/2015 | |
| WO | 2015058284 A1 | 4/2015 | |
| WO | WO-2015058284 A1 * | 4/2015 | ............ A61C 19/06 |

* cited by examiner

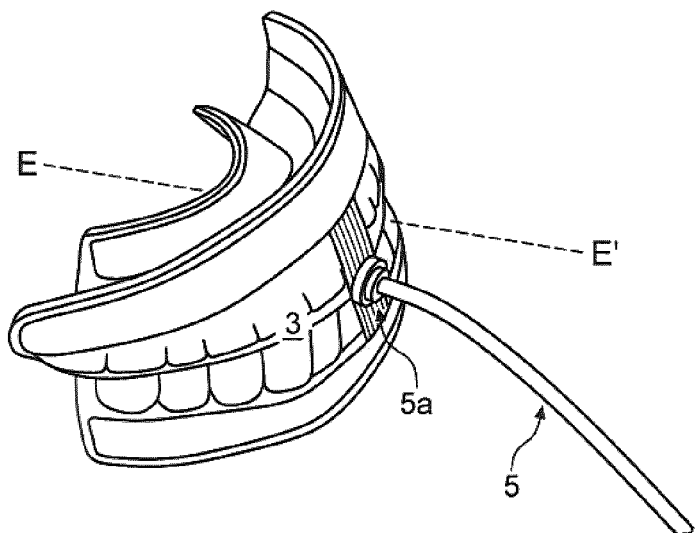
Fig. 3E
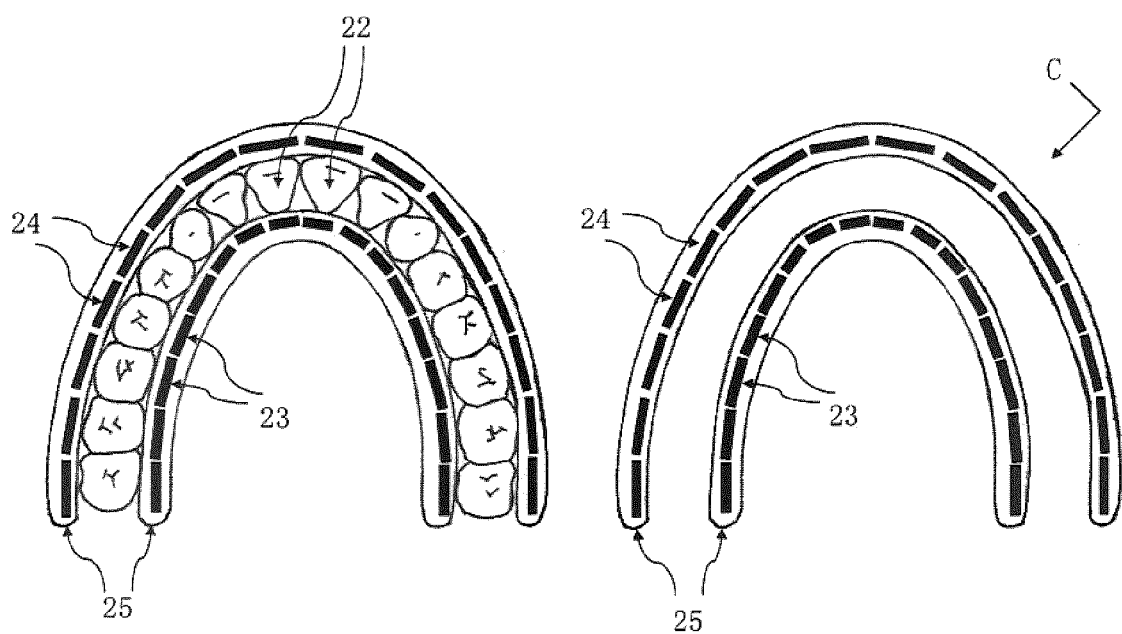
Fig. 4A  Fig. 4B

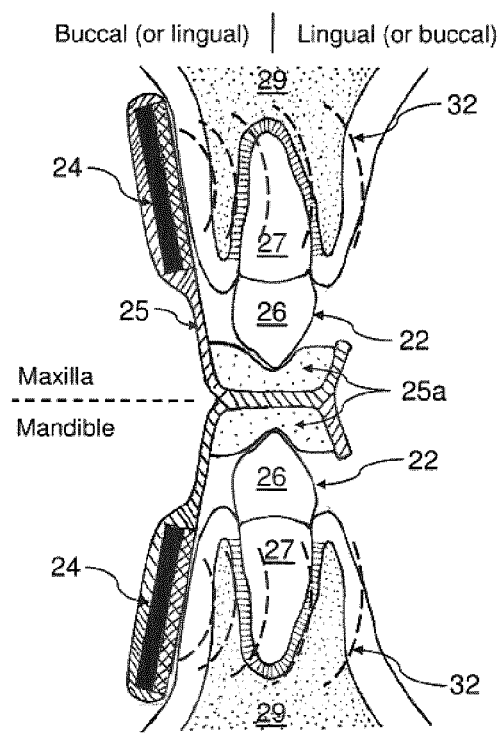
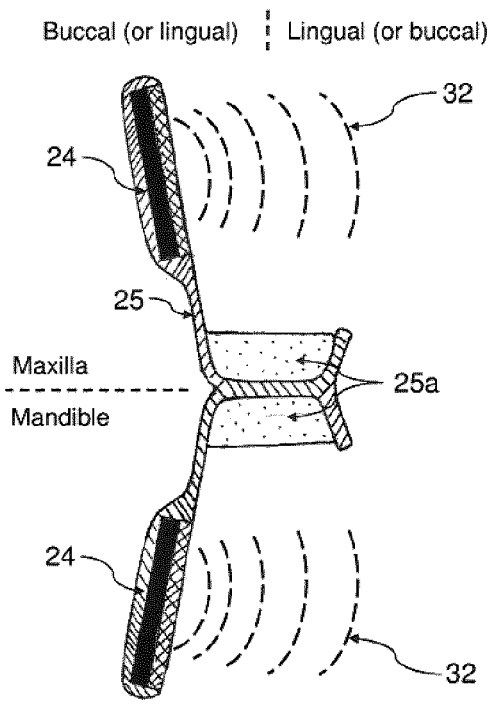
*Fig. 5I*  *Fig. 5J*

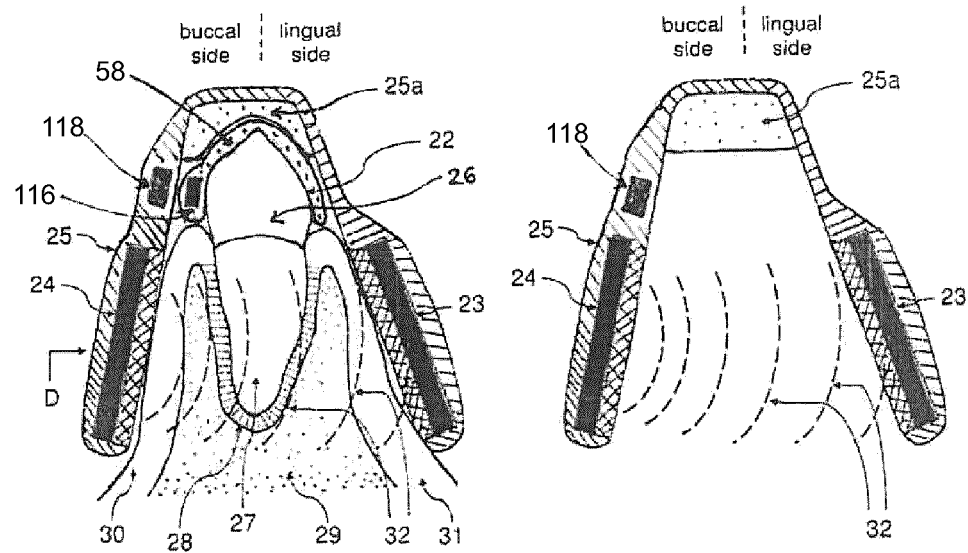
*Fig. 17A*  *Fig. 17B*
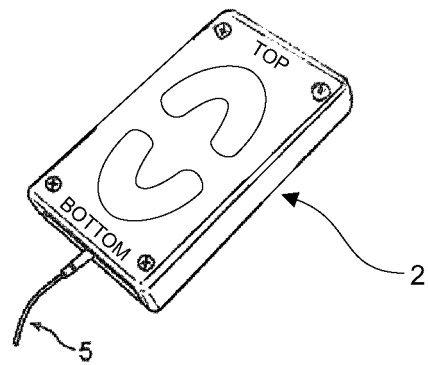
*Fig. 18*

ULTRASONIC METHODS AND DEVICES FOR ORTHODONTIC TREATMENT WITH ALIGNERS

CROSS REFERENCE TO RELATED APPLICATIONS

This application claims priority of U.S. Provisional Patent Application Ser. No. 62/447,833, entitled "Ultrasonic Methods and Devices for Orthodontic Treatment with Aligners", filed Jan. 18, 2017, and hereby incorporated by reference herein in its entirety.

TECHNICAL FIELD

This disclosure relates to ultrasound stimulation and more specifically, to methods and devices for applying ultrasound stimulation during orthodontic treatment performed with aligners.

BACKGROUND

Orthodontic aligners, such as clear aligners are orthodontic devices and systems that use sets of aligner trays, such as sets of transparent aligners, with incremental changes to adjust the position of the teeth. Similar to traditional orthodontic braces, aligners use a gradual force to control tooth movement, but without metal wires or brackets.

A set of aligners would have several different aligners to be used in a sequence. Each aligner can move teeth a small distance (a fraction of a mm), while the whole set/sequence of aligners (anywhere from several aligners to several tens of aligners, depending on treatment complexity) can move the teeth into the final desired position decided by an orthodontist. When a patient changes a clear aligner tray with the next in the sequence, different teeth may be moved by the new tray as compared with the previous aligner tray.

Currently, the acceleration of orthodontic tooth movement can be performed using ultrasound devices and methods as described in the PCT patent application No. PCT/CA2011/000498 entitled "Ultrasonic methods and device for dental treatment", hereby incorporated by reference herein. For patients with clear aligners who are utilizing an ultrasound device such as those described in PCT/CA2011/000498, acceleration can be achieved by activating all available transducers at a time, therefore accelerating the movement of all areas/teeth (the teeth to be moved as well as the anchor teeth) without any tooth or zone selectivity.

Unless a patient knows which teeth move with each aligner tray (such information is not readily available to patients from all clear aligner manufacturers) and also has access to the ultrasound device companion software or other means to change which transducers are active for which teeth or zone (such information is not commonly available to patients by the manufacturer of the ultrasound device), the patient will not be able to set the therapeutic ultrasound treatment to be activated only for the teeth to be moved for each aligner tray.

The ability to selectively accelerate the movement of some teeth and while not accelerating the movement of other teeth is important because orthodontic treatment can be composed of a sequence of tooth movements. In each sequence, the mechanical force from the orthodontic appliance (wire braces or clear aligners) can be applied in such a way to achieve the greatest amount of movement of the teeth to be repositioned and the least amount of movement of other teeth (which are used as anchors). It is known in the art that the movement of anchor teeth is undesirable, referred to as anchorage loss, and should be minimized. In many cases the lost anchorage will have to be corrected (anchors moved back) at later stages of treatment, which takes additional treatment time.

Accordingly, there remains a need to provide multiplicative treatment-duration shortening devices and methods for patients under orthodontic treatment with aligners that can overcome the shortcomings of the prior art.

SUMMARY

Devices and methods for ultrasonic dental treatment are described, specifically how the devices and methods described in PCT patent application No. PCT/CA2011/000498, incorporated by reference herein, can be modified and/or complemented in order to provide a multiplicative treatment-duration shortening for patients under orthodontic treatment with aligners, such as clear aligners.

Being able to selectively accelerate the movement of teeth to be repositioned can result in shortening the time the desired tooth is repositioned (at accelerated speed). During this shortened time, anchor teeth can move at a natural (slower) speed and, therefore, can move a lesser amount, and anchorage loss is reduced.

As a result, the orthodontic treatment can be not only shortened by moving the desired teeth faster, but the treatment can be further shortened by reducing the time required for anchorage loss correction.

In addition, an ultrasound device can reduce root resorption and discomfort from the aligner trays. Such a reduction can allow an aligner manufacturer to apply a larger orthodontic force and move teeth further with each tray. This strategy can result in even faster treatment and fewer aligner trays to be manufactured for treatment.

Broadly stated, in some embodiments, a method of orthodontic treatment is provided, the method comprising providing an orthodontic aligner to a patient to move at least one tooth to a desired location; providing treatment information comprising desired movement information of the at least one tooth; and communicating the treatment information to a system for use in emitting ultrasound to a dental area, the system comprising an intra-oral dental attachment for providing ultrasound emissions to the dental area.

In some embodiments, the methods can further comprise activating the system, based on the treatment information, to selectively target the at least one tooth, and emitting ultrasound from the intra-oral dental attachment to the dental area proximate the at least one tooth.

Broadly stated, in some embodiments, a device for orthodontic treatment is provided, the device comprising an intra-oral dental attachment for providing ultrasound emissions to a dental area; a communication module to receive treatment information comprising desired orthodontic aligner based movement information of at least one tooth; at least one ultrasound transducer configured to selectively emit ultrasound to the dental area proximate the at least one tooth pursuant to the treatment information.

Broadly stated, in some embodiments, a system for orthodontic treatment to complement and accelerate orthodontic aligner treatment is provided, the system comprising an intra-oral dental attachment for emitting ultrasound to a dental area; the dental attachment comprising at least one flexible array of cooperative ultrasound transducers for emitting ultrasound; a communication module to receive treatment information comprising desired orthodontic aligner based movement information of at least one tooth wherein the at least one flexible array of cooperative ultrasound transducers is configured to selectively emit ultrasound to the dental area proximate the at least one tooth pursuant to the treatment information; and external controlling means for controlling the ultrasound, the external controlling means being in communication with the dental attachment.

Broadly stated, in some embodiments, an orthodontic aligner for use with an intra-oral ultrasound system is provided, the orthodontic aligner comprising a body configured to move at least one tooth; and a communication module associated with the body, the communication module to communicate treatment information comprising desired orthodontic aligner based movement information of the at least one tooth to the intra-oral ultrasound system, wherein the intra-oral ultrasound system is configured to selectively emit ultrasound to a dental area proximate the at least one tooth pursuant to the treatment information.

In some embodiments, the communication of the treatment information can be performed by a communication means/module. The communication means/module can be a manual communication means/module selected from the group consisting of an identification number on the aligner and means of entering the identification number into the system, an identification number on an external document and means of entering the identification number into the system, and a scannable code and code reader and an assessment by a dentist and means of entering the assessment into the system. In some embodiments, the communication means/module can be an automatic communication means/module selected from the group consisting of a radio-frequency identification (RFID) transponder and RFID reader, a scannable code and code reader, a change in material properties of the aligner and means of reading the material properties, and a change in optical properties and means of reading the optical properties. In some embodiments, the material properties can be magnetic properties.

BRIEF DESCRIPTION OF THE DRAWINGS

FIG. 3E is a perspective view of an embodiment of an ultrasonic dental attachment for the treatment of both dental arches;

FIG. 4A is a horizontal cross-section view of the ultrasonic dental attachment shown in FIG. 3A through horizontal plane AA';

FIG. 4B is a horizontal cross-section view of the ultrasonic dental attachment shown in FIG. 3B through horizontal plane BB';

FIG. 5I is a vertical cross section view of the ultrasonic dental attachment shown in FIG. 5G modified to emit ultrasound from only one of either lingual or buccal sides only;

FIG. 5J is a vertical cross section view of the ultrasonic dental attachment shown in FIG. 5I when not placed over teeth;

FIG. 17A is a vertical cross section view of an embodiment of an ultrasonic dental attachment, with an embedded magnetic sensor, placed over teeth with a clear aligner that has embedded magnetic materials;

FIG. 17B is a vertical cross section view of the ultrasonic dental attachment of FIG. 17A, not placed over teeth, with an embedded magnetic sensor;

FIG. 18 is a perspective view of an embodiment of an external electronics controller with magnetic sensors incorporated;

DETAILED DESCRIPTION OF THE EMBODIMENTS

Ultrasonic devices, systems, and methods for orthodontic treatment performed with aligners are described. Communication of desired ultrasound treatment can be communicated from an aligner to an ultrasound device by a communication means or a communication module. Such communication means/module can use, among other things, an identification number on the aligner and means of entering the identification number into the system, an identification number on an external document and means of entering the identification number into the system, a scannable code and code reader, and an assessment by a dentist and means of entering the assessment into the system, a radio-frequency identification (RFID) transponder and RFID reader, a change in material properties of the aligner and means of reading the material properties, or a change in optical properties and means of reading the optical properties.

Figure 1:
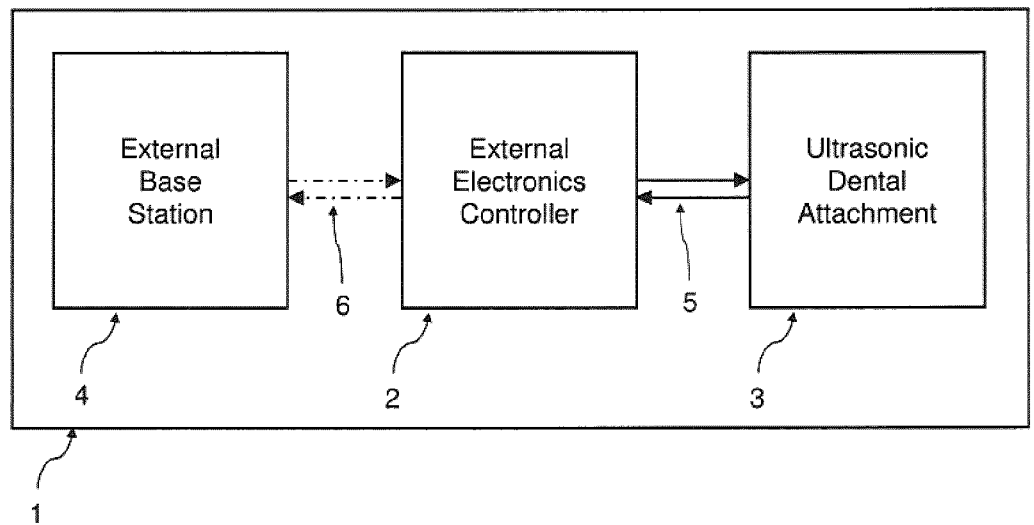
FIG. 1 is a block diagram of an embodiment of an ultrasonic dental system.

Referring now to FIG. 1, an embodiment of an ultrasonic dental system 1 can include an external electronic controller 2, an ultrasonic dental attachment 3, and an external base station 4. External base station 4 can be a personal computer, a smart phone, or other smart device, that can connect to the external electronic controller 2 though temporary, bidirectional communication, connection 6. Temporary connection 6 can be made through a wired means (for example, a cable) or a wireless means (for example, radio, infrared, or magnetic). External base station 4 can use a software application 101 (also referred to as ultrasound device companion software) to interact with the external electronic controller 2.

External base station 4 can be used to program the ultrasonic dental system 1, download and read recorded treatment data and ensure treatment compliance, service or repair ultrasonic dental system 1, or charge the battery of external electronics controller 2 for instance by providing electrical power from the USB port of the personal computer. Battery of external electronics controller 2 could also be charged by means of a plug-in adapter (not shown).

External electronic controller 2 can be connected to ultrasonic dental attachment 3 through a fixed, bidirectional communication, connection 5. Fixed connection 5 can be a flexible multi wire cable, in some embodiments.

Ultrasonic dental system 1 can also include a storage/travel box (not shown) to store ultrasonic dental attachment 3. The storage/travel box can also include a tray and solution for cleaning, disinfection and storage.

Figure 2:
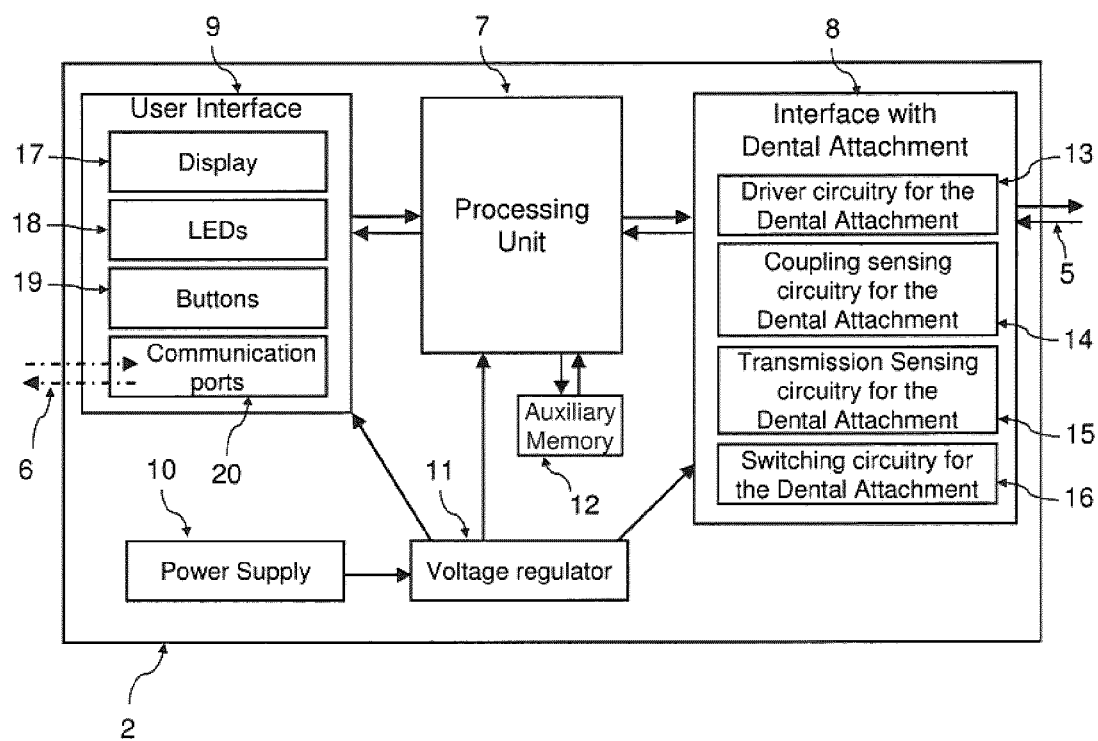
FIG. 2 is a block diagram of an embodiment of an external electronics controller of the system shown in FIG. 1.

Referring now to FIG. 2, external electronics controller 2 can be made using off-the-shelf electronic components, custom designed printed circuit board(s), and custom developed firmware. External electronics controller 2 can include a processing unit 7, a dental attachment interface 8, a user interface 9, a power supply 10, and a voltage regulator 11.

Processing unit 7 can be microcontroller such as an AVR 8-bit microcontroller, for example ATmega 2560, and can also include auxiliary memory 12. Interface 8 can connect external electronics controller 2 to ultrasonic dental attachment 3 through connection 5. Interface 8 can also include driver circuitry 13, coupling sensing circuitry 14, transmission sensing circuitry 15, and switching circuitry 16, for ultrasonic dental attachment 3. User interface 9 can include a display or touch screen 17, light emitting diodes (LEDs) 18, user buttons 19, and one or more communication ports 20. Communication ports 20 can be connected with the external base station 4 through temporary connection 6. Power supply 10 can be a battery (rechargeable or not-rechargeable), a charger for the battery, or a wall plug-in electric adapter. Communication ports 20 can also include charging features for power supply 10.

External electronic controller 2 can connect wirelessly or wired to another electronic device such as smart phone or other smart device. The smart device may act as some of the components of the external electronic controller 2 such as the user interface 9. In this case the external electronic controller 2 could be a module that attaches to the smart device for example, and the smart device can use an application software program to power and control the external electronic controller 2 which can control the ultrasonic dental attachment 3.

Referring now to FIGS. 3A, 3B, 3C, 3D, 4A, and 4B, ultrasonic dental attachment 3 can include interior ultrasound transducers 23 on the lingual side of a patient's teeth 22 and exterior ultrasound transducers 24 on the buccal side of teeth 22. There can be sixteen teeth on each dental arch (mandible and maxilla) and there can be one interior transducer 23 on the lingual side of each tooth 22. In some embodiments one transducer can cover more than one tooth. In some embodiments, more than one transducer can cover the buccal side of a tooth and/or the lingual side of a tooth. In some embodiments, not all teeth are covered. In embodiments having one transducer per tooth, sixteen interior transducers 23 on the lingual side of each dental arch can form a flexible array of transducers. In some embodiments, this array can be linear or curved. In some embodiments, the array can comprise cooperative ultrasound transducers which can cooperate during ultrasound treatment. There can be one exterior transducer 24 on the buccal side of each tooth 22 and there can be sixteen exterior transducers 24 on the buccal side of each dental arch forming a flexible array of transducers. In some embodiments, this array can be linear or curved. Flexible enclosure 25 can encase transducers 23, 24 and can cover the crown and root of the tooth. Flexible enclosure 25 can be made of plastic polymers such as polypropylene, copolyester or ethyl vinyl acetate (EVA) or silicone. In one embodiment, two separate ultrasonic dental attachments 3 can be used interchangeably or simultaneously for the mandible and maxilla.

Referring now to FIG. 3E, in another embodiment, two arches (one for mandible and one for maxilla) can be formed together into an ultrasonic dental attachment 3 that can treat both dental arches. As illustrated in FIG. 3E, ultrasonic dental attachment 3 can include four flexible arrays of ultrasound transducers 23, 24: one array for maxillary buccal side, one for the maxillary lingual side, one for the mandible buccal side, and one for mandible lingual side. The ultrasonic dental attachment 3 can have orifices in the occlusion (bite section) of the dental attachment 3 to allow patient breathing.

Figure 3A:
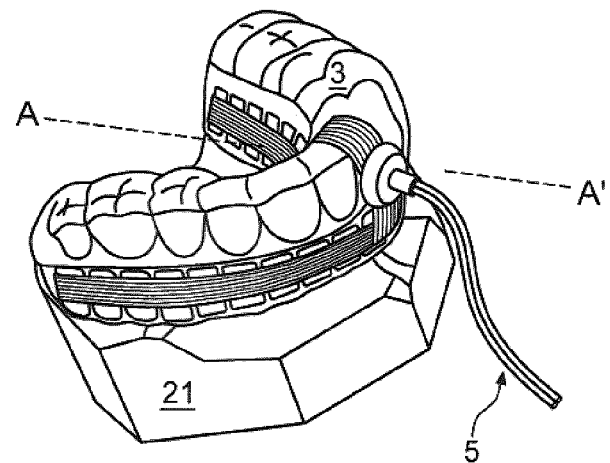
FIG. 3A is a perspective view of an embodiment of an ultrasonic dental attachment with an embedded connector placed on a dental cast.
Figure 3B:
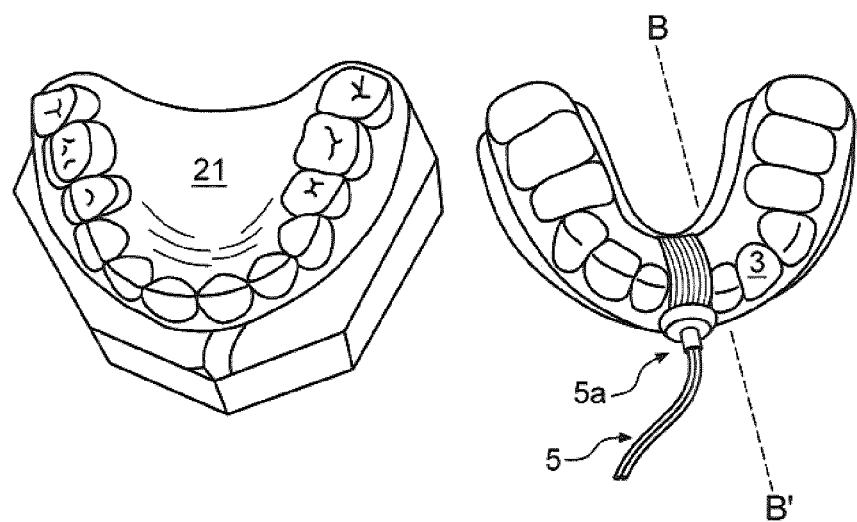
FIG. 3B is a top view of an embodiment of the ultrasonic dental attachment of FIG. 3A placed beside the dental cast.
Figure 3C:
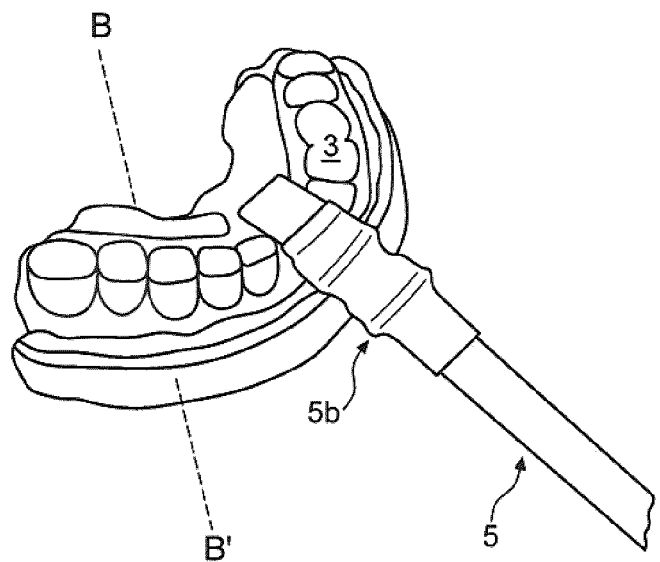
FIG. 3C is a perspective view of an embodiment of the ultrasonic dental attachment with an external connector.
Figure 3D:
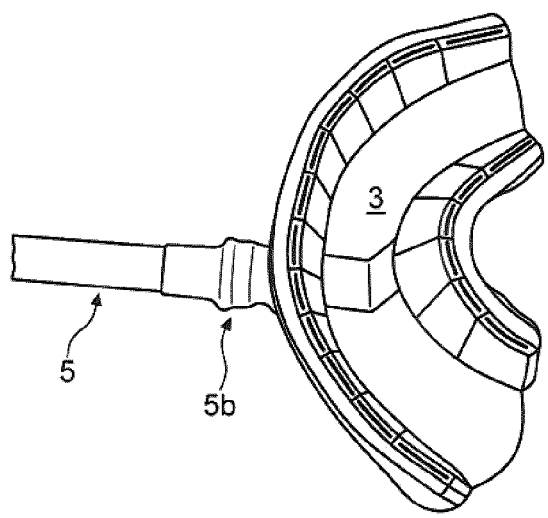
FIG. 3D is a bottom view of an embodiment of the ultrasonic dental attachment with an external connector.

As in FIG. 3A, dental cast 21 can be used for illustrating how the ultrasonic dental attachment 3 can fit on patient teeth 22. Ultrasonic dental attachment 3 can be similar to a mouthguard. Professional alignment or adjustment of the position of the device is not necessarily required. The patient can bite down on ultrasonic dental attachment 3 in order to keep it positioned well on the teeth 22 during treatment and ensure the placement is consistent with each use.

Connection 5 is shown as a cable which can connect ultrasonic dental attachment 3 to external electronics controller 2. In some embodiments, connection 5 can include wires and embedded connector 5a water-sealed inside the ultrasonic dental attachment (FIG. 3A, 3B, 3E), or external connector 5b (FIGS. 3C and 3D) as an extension of the ultrasonic dental attachment 3. Connectors 5a or 5b can connect transducers 23, 24 from ultrasonic dental attachment 3 to the external electronics controller 2 as desired through connection cable 5.

In addition, the connectors 5a and 5b can be permanently attached or can be disconnected when cleaning, replacing or servicing of intra-oral attachment 3 is required.

Figure 5A:
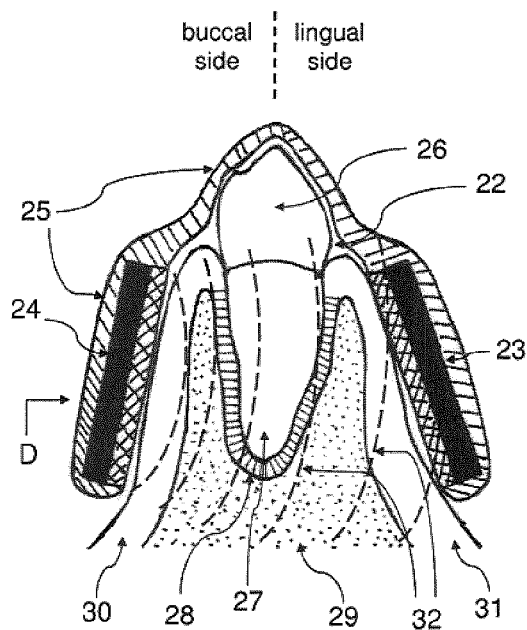
FIG. 5A is a vertical cross-section view of the ultrasonic dental attachment shown in FIG. 3A through points AA'.
Figure 5B:
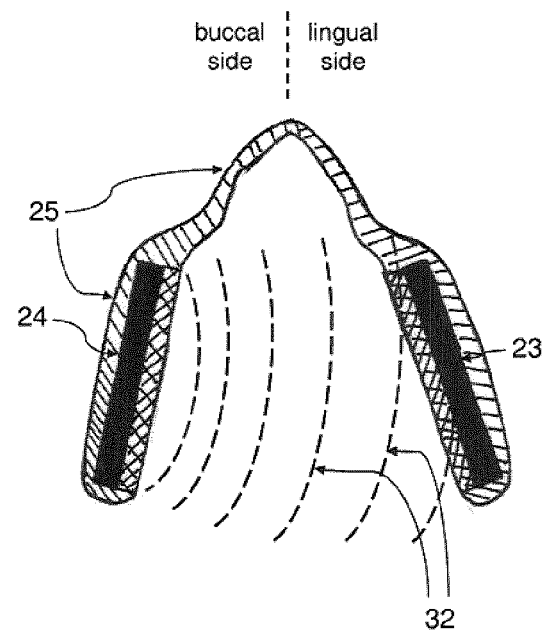
FIG. 5B is a vertical cross-section view of the ultrasonic dental attachment shown in FIG. 3B through points BB'.

Referring now to FIGS. 5A and 5B, tooth 22 can include crown 26 and root 27. Tooth 22 can be connected through periodontal ligaments 28 to alveolar bone 29. Gums, or gingiva 30,31, can envelope alveolar bone 29 on the buccal side 30 and on the lingual side 31 of tooth 22.

In one embodiment, ultrasound waves 32 can be propagated from the buccal side transducer 24 through flexible enclosure 25, buccal side gums 30, alveolar bone 29, periodontal ligaments 28, tooth root 27, and can continue propagation through periodontal ligaments 28, alveolar bone 29, lingual side gums 31, flexible enclosure 25 on the lingual side of tooth 22 and finally can enter the lingual transducer 23 where ultrasound wave 32 can be converted into an electric signal.

Ultrasonic dental attachment 3 can use coatings or layers between gums 30, 31 and transducers 23, 24 that can behave as antireflection layers for the ultrasound waves 32 at an operating frequency. The thickness of the coatings can be an odd multiple of quarter wavelengths of an ultrasound wave 32 in that material. This thickness can allow improved coupling of ultrasound waves 32 from the emitter to the tissues and from the tissues to the sensor and also can reduce the reflections back to the emitter or sensor which can cause noise in ultrasonic dental system 1 and wave interference that can affect treatment outcomes.

Flexible enclosure 25 can be made of flexible materials such as polypropylene, copolyester, ethyl vinyl acetate (EVA), or silicone which can be thermally formed, injection molded, deposited, or applied over and around transducers 23, 24 in order to seal them from the external factors such as the saliva from the patient or humidity from the environment. Such layers of flexible materials can have thickness of less than 1 mm while maintaining good strength and sealant properties.

In this example, buccal side transducer 24 can emit ultrasonic waves, while the lingual side transducer 23 can receive and sense ultrasonic waves 32, although it would be appreciated that the opposite could also occur. In this scenario, transducer 24 works as an emitter and transducer 23 as a transmission sensor. In order to expose the tooth root 27 or crown 26 to uniform ultrasonic treatment (uniform ultrasonic intensity), the transducers 23, 24 from the buccal and lingual side can interchange their dual function of emitting and sensing. For instance, during a further step in treatment, transducer 23 can emit ultrasound waves 32 and transducer 24 can sense the transmitted ultrasound waves 32. In this way ultrasonic waves can equally expose tooth 22 from both sides.

When multiple ultrasound emitters are used at the same time in proximity to each other, wave interference can occur which can reduce the dental treatment outcome or can also cause tissue damage. The amplitude and location of wave interference patterns can be difficult to predict and control as each patient has a unique dental structure. Ultrasonic dental system 1 can be configured so that transducers 23, 24 will not emit ultrasound waves 32 at the same time. As such, ultrasonic dental system 1 can avoid the interference of the ultrasonic waves 32 inside tissues 27, 28, 29, 30, 31.

In one embodiment, transducer 23, 24 can cover the entire length (or a large portion) of root 28, from the gum-crown interface to the tip of the root. By using a transducer that covers the root 28, it can be possible to treat dental problems located at any point of root 28 including its tip, or treat the alveolar bone 29 all around the root and its tip. Applications can include healing dental implants, root resorption, periodontitis, and accelerating alveolar bone remodeling.

The area and shape of transducers 23, 24 can vary from tooth to tooth and from buccal side to the lingual side of a tooth 22. Transducers 23, 24 can have different shapes (rectangular, trapezoids, ovals, circular, etc), with different widths, heights, or radii. In some embodiments, the width of transducers 23, 24 can be similar with the width of a tooth crown 26, while the height can be similar with the length of the root 27. As the width of tooth 22 and the length of root 27 varies from tooth to tooth (for example incisors have a smaller crown 26 width but a longer root 27 than a molar), transducers 23, 24 can have different widths and heights.

Figure 5C:
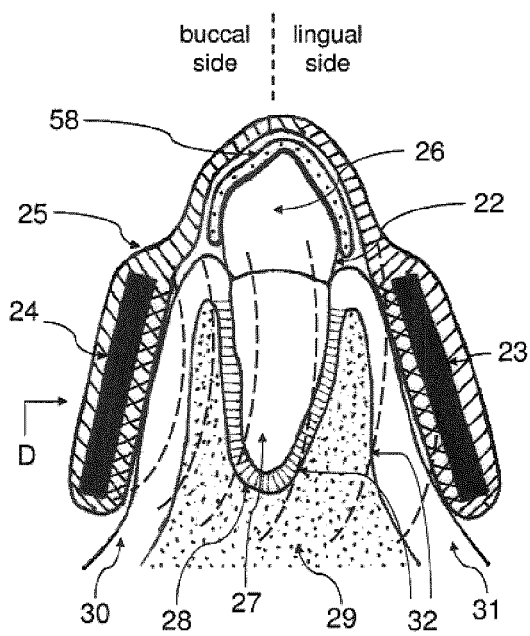
FIG. 5C is a vertical cross-section view of the ultrasonic dental attachment shown in FIG. 3A through points AA' where the ultrasonic dental attachment has been modified to accommodate a clear orthodontic aligner or retainer.
Figure 5D:
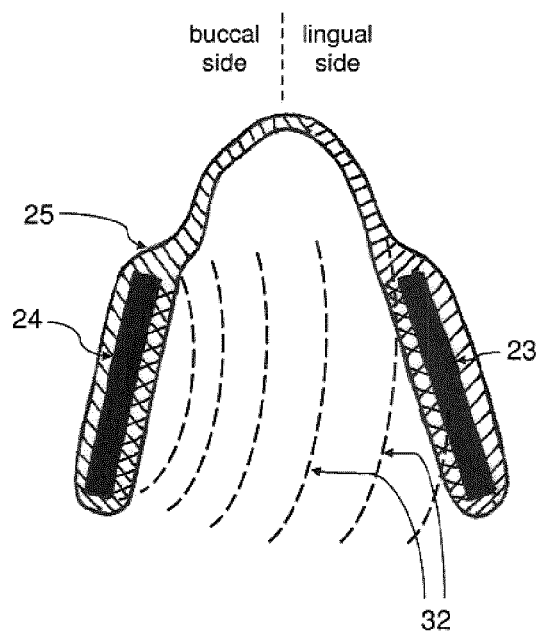
FIG. 5D is a vertical cross-section view of the ultrasonic dental attachment shown in FIG. 3B through points BB' where the ultrasonic dental attachment has been modified to accommodate a clear orthodontic aligner or retainer.

Referring to FIGS. 5C and 5D, an embodiment of ultrasonic dental attachment 3 can be designed to accommodate a clear orthodontic aligner or retainer 58.

Figure 5E:
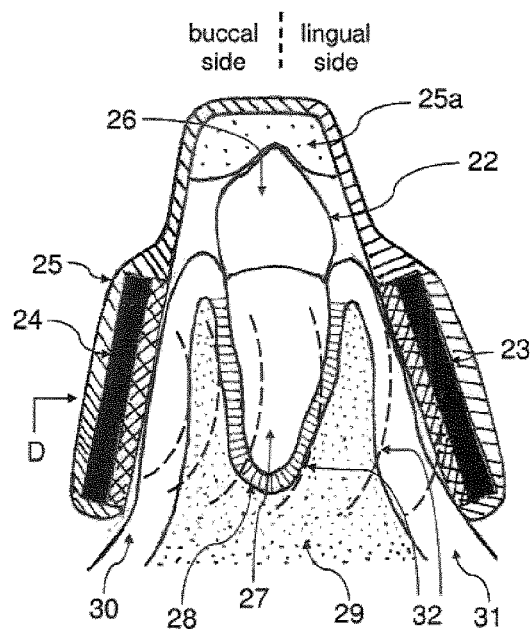
FIG. 5E is a vertical cross-section view of the ultrasonic dental attachment shown in FIG. 3A through points AA' where the ultrasonic dental attachment has been modified to accommodate a soft bite pad.
Figure 5F:
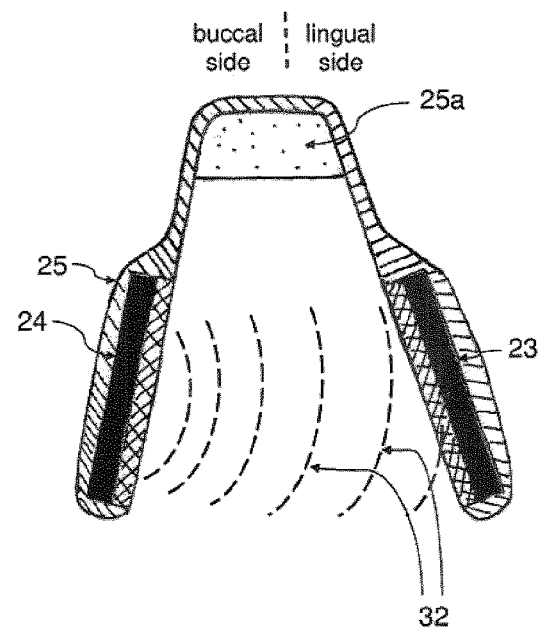
FIG. 5F is a vertical cross-section view of the ultrasonic dental attachment shown in FIG. 3B through points BB' where the ultrasonic dental attachment has been modified to accommodate a soft bite pad.

Referring now to FIGS. 5E and 5F, a further embodiment of ultrasonic dental attachment 3 can be designed to have a general form of a dental tray. In some embodiments, the interior of the tray (facing tooth crown 26) can be filled with soft bite pad 25a which can be made of a malleable material. As an example, soft bite pad 25a can be made of silicone. Therefore, when the patient bites attachment 3, soft bite pad 25a can reshape and accommodate tooth crowns 26. If the positions of the teeth change over time (such as during orthodontic treatment), soft bite pad 25a can allow continuous fit over tooth crowns 26. An embodiment of the ultrasonic dental attachment 3 can accommodate any type of orthodontic appliance (for example, wire braces and clear orthodontic aligners). As illustrated in FIG. 5F, soft bite pad 25a can recover its original shape when not bitten.

Figure 5G:
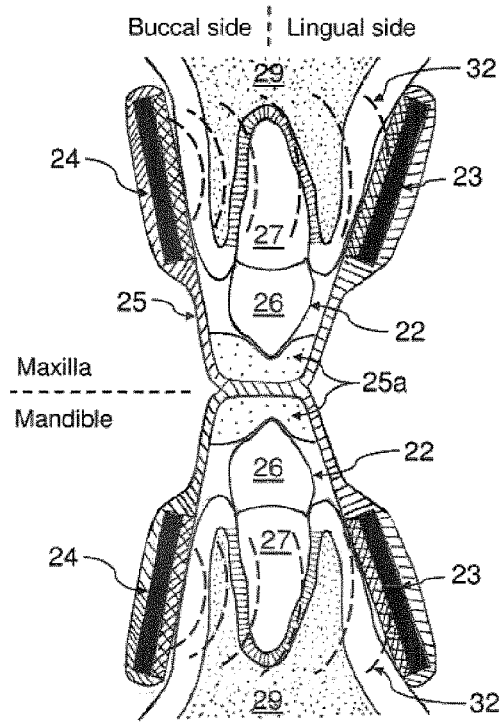
FIG. 5G is a vertical cross section view of the ultrasonic dental attachment shown in FIG. 3E through points EE and placed over teeth, where the ultrasonic dental attachment has been modified to fit both dental arches (maxilla and mandible)
Figure 5H:
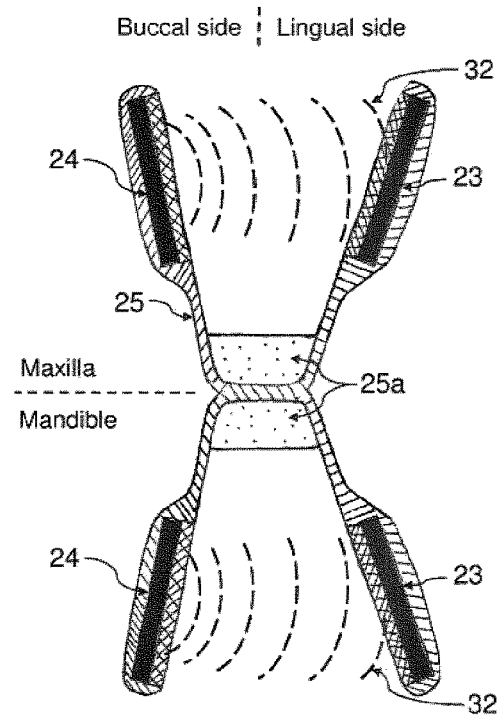
FIG. 5H is a vertical cross section view of the ultrasonic dental attachment shown in FIG. 5G when not placed over teeth.

Referring now to FIGS. 5G and 5H, in some further embodiments, ultrasonic dental attachment 3 can be designed to fit both dental arches (maxilla and mandible). Some embodiments can deliver ultrasonic treatment selectively to tooth roots 27 from both dental arches (maxilla and mandible) and from both lingual and buccal directions as desired, while using a single external electronics controller 2.

Referring now to FIGS. 5I and 5J, some embodiments of ultrasonic dental attachment 3 can be designed to fit both dental arches (maxilla and mandible), and deliver the ultrasonic treatment selectively to tooth roots 27 from both dental arches (maxilla and mandible) from one direction only (lingual or buccal) using a single external electronics controller 2.

FIGS. 5G, 5H, 5I and 5J illustrate examples of ultrasonic dental attachments that can treat both dental arches (maxilla and mandible): from both lingual and buccal directions (FIGS. 5G and 5H), and from one direction only (FIGS. 5I and 5J). The embodiments in FIGS. 5I and 5J can be made to attach and emit ultrasound to the lingual side of the teeth or to the buccal side of the teeth, as required for treatment. For instance, people wearing customized orthodontic appliances such as space closing springs or temporary anchorage screws, some embodiments of the ultrasonic dental attachment may physically interfere with the springs or anchorage screws and it is desired to use an ultrasonic dental attachment that has the ultrasonic transducers on the side opposite of the springs or screws. In addition, FIGS. 5G, 5H, 5I and 5J illustrate examples where the soft bite pad 25a can be used, but orifices can also be used to accommodate orthodontic brackets, or extra space for clear aligners 58 (as shown in FIG. 5C) could also be used, or a tighter fit as illustrated in FIG. 5A could also be used, or any combination of the above.

To allow for good coupling of the ultrasonic waves to teeth (crowns and gums), in some embodiments, a coupling agent can be applied to the tooth/gum contacting surface of ultrasonic dental attachment 3 when treatment is to be applied. A coupling agent can also be used between ultrasonic dental attachment 3 and aligner 58. In some embodiments, the coupling agent can be ultrasonic gel. In some embodiments, the coupling agent can be water or a water-soaked substrate. It would be understood by a person skilled in the art that any material which functions as a suitable coupling agent can be used.

Figure 6:
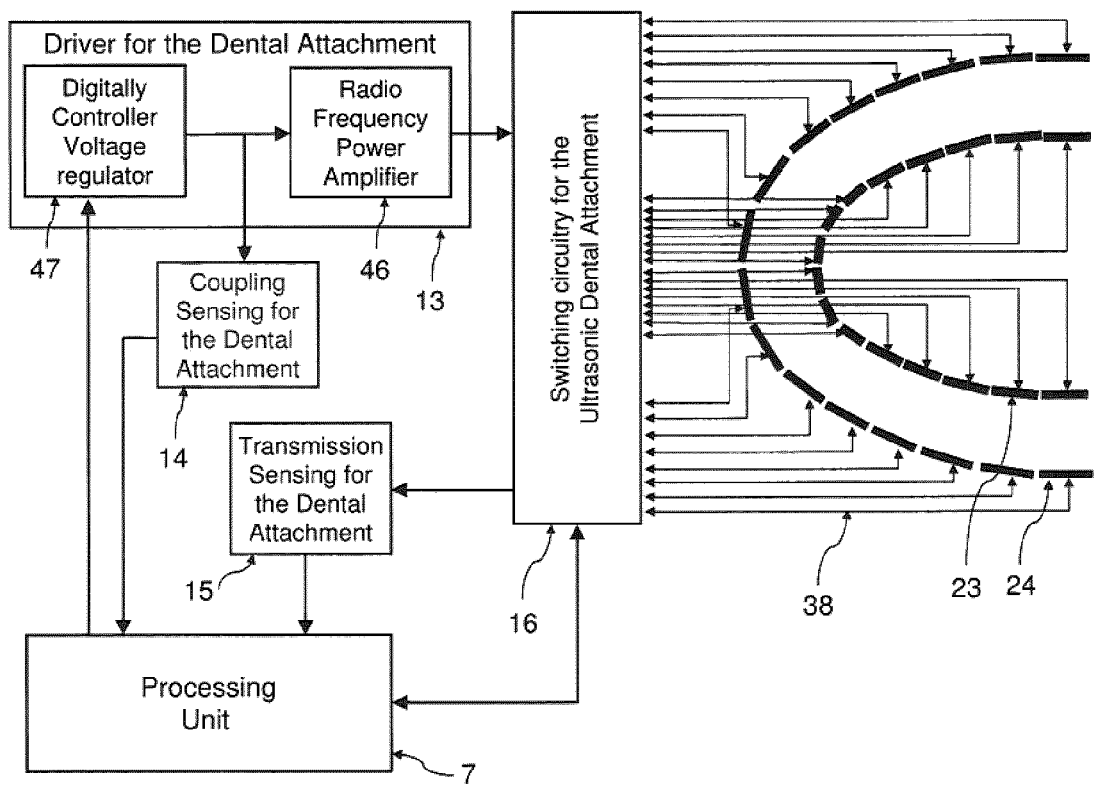
FIG. 6 is a block diagram of an embodiment of a circuitry interface with an ultrasonic dental attachment.

Referring now to FIG. 6, an embodiment of circuitry interface 8 from FIG. 2 is shown with ultrasonic dental attachment 3 circuitry. Driver 13 can include at least one radio frequency (RF) power amplifier 46 and at least one digitally controlled voltage regulator 47. Voltage regulator 47 can be a variable voltage regulator controlled by a digital potentiometer, where the digital potentiometer can be controlled by the processing unit 7. Coupling sensing circuitry 14 can be made of a current sense circuitry that can monitor the DC current supplied by digitally controlled voltage regulator 47 to RF Power amplifier 46. The output of coupling sensing circuitry 14 can be read by an Analogue to Digital Converter (ADC) port of the processing unit 7 which can be a microcontroller.

Transmission sensing circuitry 15 can be a full-wave (or half-wave) rectifier circuitry such as bridge rectifier or diode less rectifiers, followed by an envelope detector. The output of transmission sensing circuitry 15 can be read by an Analogue to Digital Converter (ADC) port of the processing unit 7 which can be a microcontroller. Switching circuitry 16 can be located in external electronic controller 2 or in ultrasonic dental attachment 3, or a portion in controller 2 and another portion in dental attachment 3. In some embodiments, a portion of switching circuitry 16 could also be located on the cable 5 or connector 5a or 5b.

Information relating to the teeth or zones to be treated with ultrasound can be communicated by a communication means or communication module from aligner 58 to system 1. Once system 1 receives the information on what zones to activate, the processing unit 7 can send an electric signal to the switching circuitry 16 for the ultrasonic dental attachment 3, which can activate the desired zones. At the same time, the processing unit 7 can send an electric signal to the driver 13 for the dental attachment 3, which can send the output signal to the switching circuitry 16 for the ultrasonic dental attachment 16. It should be noted that the driver 13 for the dental attachment 3 and switching circuitry 16 for the ultrasonic dental attachment 3 can be separate chips or a single chip.

Figure 7A:
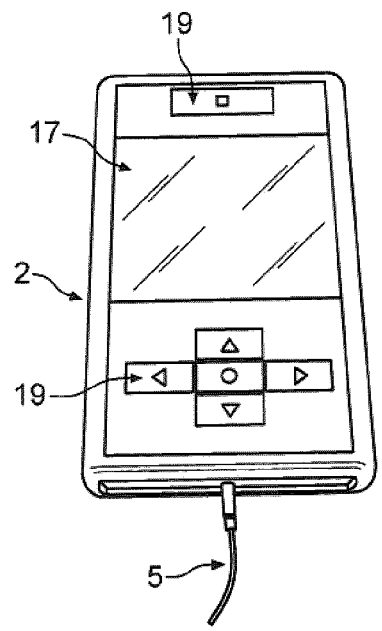
FIG. 7A is a front view of an embodiment of an external electronics controller.
Figure 7B:
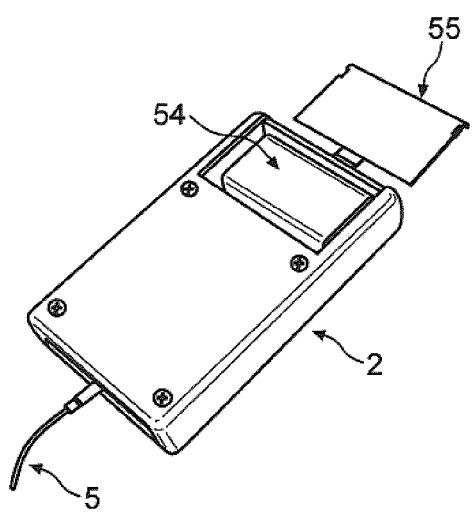
FIG. 7B is a rear view of an embodiment of an external electronics controller.

Referring now to FIGS. 7A and 7B, a front and rear view of an embodiment of external electronics controller 2 are shown. The front panel of external electronics controller 2 can have user interface elements such as display 17 (LCD or touch screen) and push buttons 19 which can allow a user (patient or dental professional) to operate and interact with ultrasonic dental system 1. External electronics controller 2 may also include a speaker (not shown).

In some embodiments, a user can turn on/off the device using the button 19, can receive information on the treatment status from display 17, and can be alerted by display 17 and speaker if there is a malfunction or a low power level. External electronics controller 2 and its interface can allow the setting of the ultrasonic dental system 1 prior to ultrasonic treatment. A user can turn on only the emitter-sensor pairs for the teeth that have to be treated and not treat healthy teeth. In some embodiments external electronics controller 2 can record treatment data which can be later verified by the user in order to ensure treatment compliance and improve treatment outcomes.

External electronics controller 2 can be battery powered or powered from the wall using a plug-in adapter. The rear panel of external electronics controller 2 can provide access to battery 54. Battery compartment can be covered by cover 55. The rear panel of external electronics controller 2 can also provide access to a connection port such as USB (for connection to a computer) or connector for power supply or battery charging.

In some embodiments, ultrasonic dental system 1 can provide a method to accelerate the orthodontic tooth movement without applying any additional force (cyclical and/or continuous) to a tooth crown. The application of ultrasound dental treatment as described herein can result in accelerated orthodontic tooth movement while not affecting the amount and direction of the forces applied by the orthodontic appliance (such as wire braces or clear aligners) to the tooth crowns. The application of ultrasound can affect the speed of tooth movement by accelerating the processes involved in the alveolar bone remodeling around the tooth roots. The use of ultrasonic dental system 1 can eliminate the need for temporary anchorage devices for orthodontic tooth movement and space closure as it selectively accelerates only the teeth of interest and not the anchorage teeth. The use of ultrasonic dental treatment, for example through ultrasonic dental system 1, can increase the movement ratio between target tooth and anchorage tooth.

Figure 8:
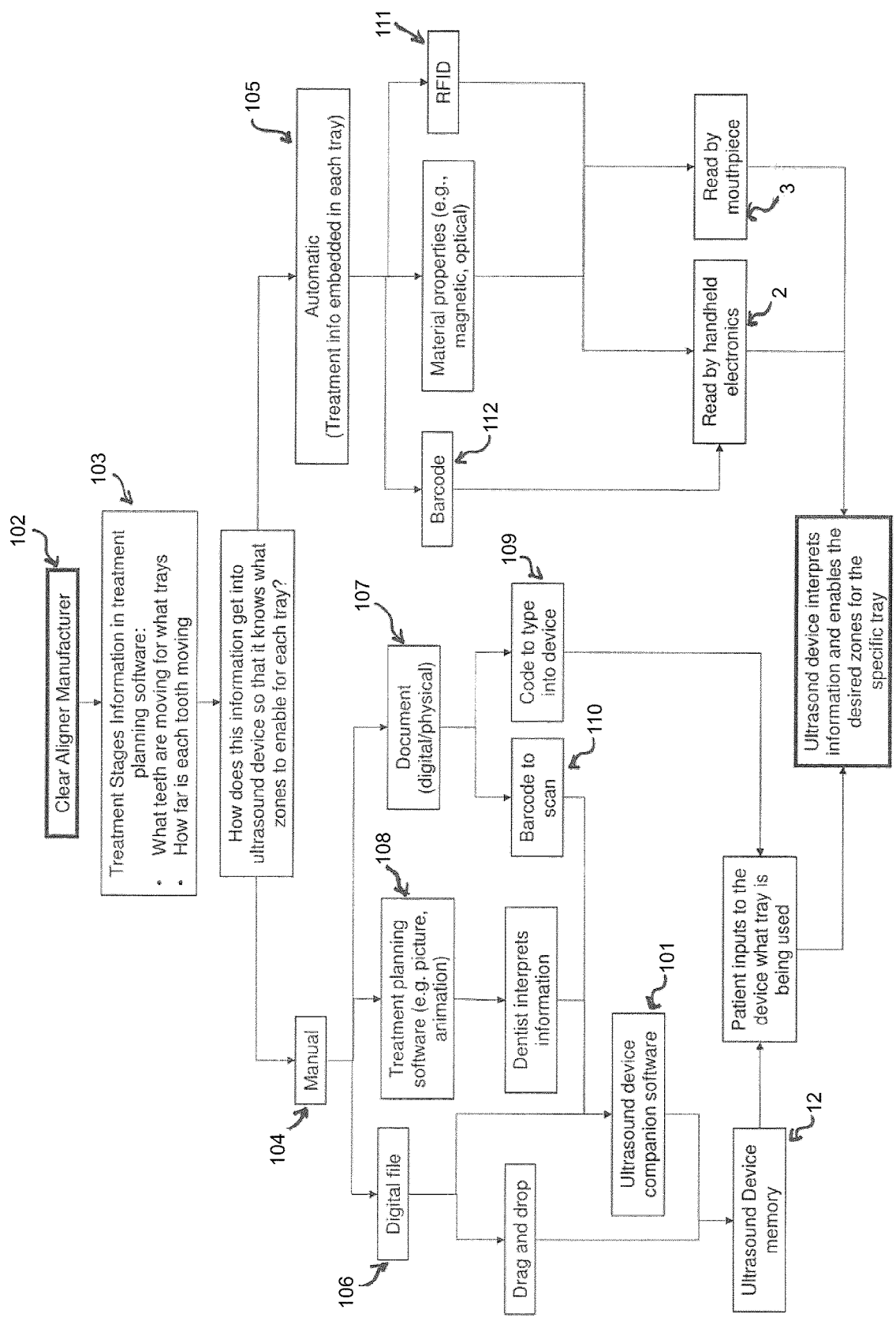
FIG. 8 is process flowchart of an embodiment of a method disclosed herein.
Figure 9:
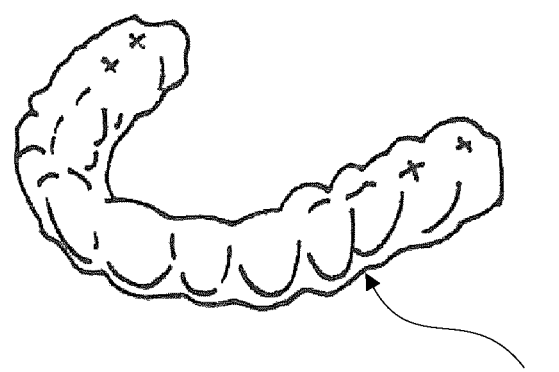
FIG. 9 is a perspective view of an embodiment of a clear aligner tray.

Referring to FIG. 8, as part of an orthodontic treatment with aligners, the dentist or orthodontist can provide desired final positions of a patient's teeth to a clear aligner manufacturer. Using this information, the clear aligner manufacturer 102 and the dentist or orthodontist can plan the treatment stages for the patient. Each treatment stage can involve a single clear aligner tray 58 that can be configured to move a specific tooth 22 or group of teeth. FIG. 9 shows an example of a common clear aligner tray. For each treatment stage 103, it can be known what is desired regarding which teeth are to be moved and how far each tooth is to be moved.

The ultrasound devices described in PCT patent application No. PCT/CA2011/000498 can provide for the ability for the dentist to selectively enable and disable individual treatment zones. As described in PCT/CA2011/000498, a treatment zone can be a tooth, a portion of a tooth, or a group of adjacent teeth. This can allow a dentist to selectively accelerate just the teeth that are to be moved during each treatment stage. What was previously unknown and undescribed are the means and mechanisms as to how to selectively target and accelerate tooth movement during an orthodontic treatment with aligners. The methods and systems herein can also apply to other stimulation devices that could provide selective emissions (ultrasound, light, vibrations, heat, or other forms of stimulation energy) for treatment to specific teeth or zones.

FIG. 8 shows an embodiment of a process flowchart representing embodiments of the methods and systems described herein and of how the treatment stage information can get from clear aligner manufacturer 102 to the ultrasound device 1 (also referred to as ultrasound dental system) so that the device knows what treatment zones to enable for each clear aligner tray 58. Such a system can be especially useful as the patients commonly change several trays by themselves at home during the time interval between orthodontic clinic visits.

Two branches of methods for approaching the solution to this problem are depicted in FIG. 8: manually 104 or automatically 105 transferring the relevant information into the ultrasound device 1.

In the case of manual methods 104, a patient can be ultimately responsible for manually inputting into the ultrasound device 1 what tray 58 is being used. This input can be in the form of the tray number or a code that is translated by the ultrasound device into what treatment zones are to be enabled for ultrasound emission.

In one example, a digital file 106 can be created that includes all the required information about what treatment zones are to be enabled for ultrasound treatment for each clear aligner tray. For example, this digital file can be created directly by the clear aligner manufacturer during the treatment planning stage. Possible ways to transfer this file to the dentist include through treatment planning software 103, via physical media (e.g., flash drive, optical disc (CD, DVD, blu-ray)), e-mail, cloud storage, or other data/file sharing methods. Once the dentist has the digital file, it can be transferred to the ultrasound device memory 12. Communication or transfer methods include plugging the physical media (e.g., flash drive) directly into ultrasound device 1 and enabling the transfer directly to the ultrasound device, a wired or wireless (e.g., Bluetooth, Wi-Fi) connection to the dentist's computer (e.g., drag and drop the file onto the device as if it were a flash drive connected to computer, transfer from the ultrasound device's companion software 101). Each tray can be provided to the patient with an identification number printed on the tray, tray bag, or tray box. Ultimately, the patient can then manually input into the ultrasound device 1 the clear aligner tray 58 number that is currently being used. The ultrasound device 1 can then enable the desired ultrasound treatment zones for that specific aligner tray according to the properties/information linked to the identification number.

In another example, a document 107 (either physical or digital) can be provided by the clear aligner manufacturer 102 that can include all the required information about what treatment zones are enabled for each clear aligner tray. For each clear aligner tray, a code 109 can be provided. This code could be input into the ultrasound device by the patient. The ultrasound device can interpret this code and enable the desired ultrasound treatment zones for that specific clear aligner tray 58.

Alternatively, a scannable code 110, such as a barcode can be provided on the document for each clear aligner tray. A scannable code can be an optical, machine-readable, representation of data, or link to data, which can describe something about the object that carries the code. In this case, the barcode can include information such as which teeth 22 are to be moved by that specific tray 58. Code types that could include linear barcodes (e.g. Universal Product Code (UPC) barcode) or matrix barcodes (e.g. QR code). The code could be scanned by the dentist which would load the desired treatment zones into the ultrasound device companion software 101, which could then be transferred to the ultrasound device 1. The patient can then manually input into the ultrasound device 1 the clear aligner tray number that is currently being used. The ultrasound device can then enable the desired ultrasound treatment zones for that specific aligner tray according to the properties/information linked to the scannable code.

Figure 19:
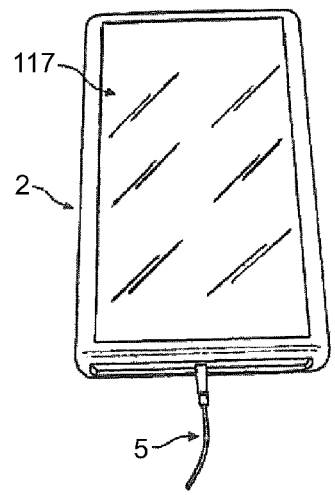
FIG. 19 is a front view of an embodiment of an external electronics controller with a touchscreen.

In yet another example, the treatment information can come to the dentist in the clear aligner manufacturer's treatment planning software 108 (e.g., picture, animation). The dentist can then interpret the information and decide what treatment zones should be enabled to best suit each treatment stage. The dentist can manually program the enabled zones for each clear aligner tray (e.g., through the ultrasound device companion software 101, directly into the ultrasound device 1 through buttons 19 or touchscreen 117). FIG. 19 shows an example of the handheld electronics 2 with a touchscreen 117. The patient can then manually input into the ultrasound device 1 the clear aligner tray number that is currently being used. The ultrasound device can then enable the desired ultrasound treatment zones for that specific clear aligner tray according to the properties/information from the dentist.

In the case of automatic methods 105, in some embodiments, the treatment information can be embedded into each clear aligner tray 58. The treatment information can then be read and interpreted by the ultrasound device 1 (e.g., by handheld electronics 2 (also referred to herein as external electronics controller)), mouthpiece 3 (also referred to herein as ultrasonic dental attachment)) and the desired ultrasound treatment zones can then be enabled for that specific clear aligner tray.

Figure 10:
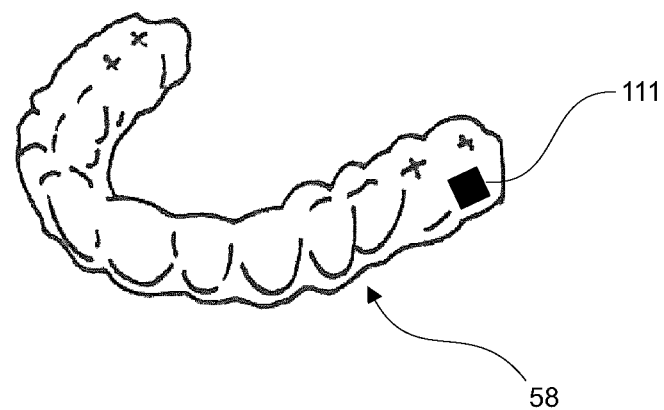
FIG. 10 is a perspective view of an embodiment of a clear aligner tray with an embodiment of an embedded radio-frequency identification (RFID) transponder.
Figure 11:
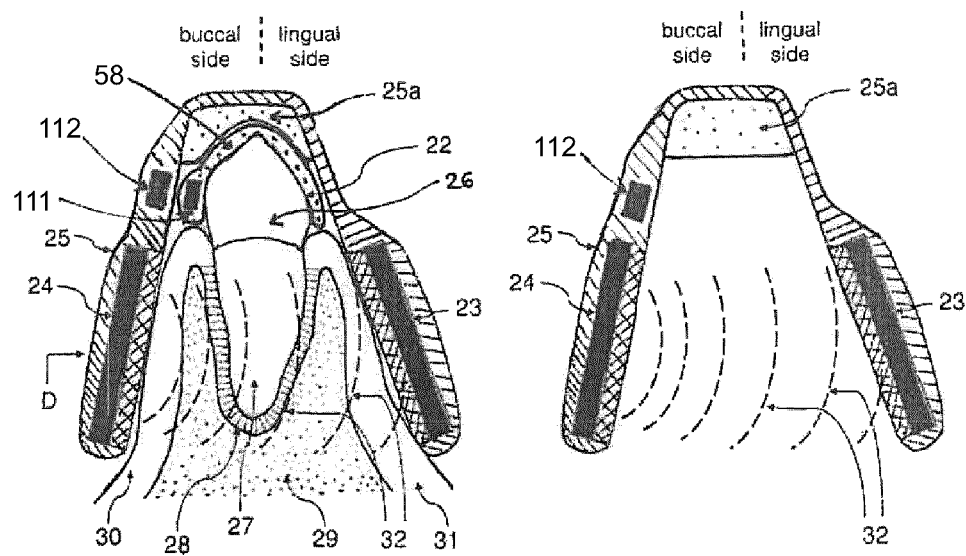
FIG. 11A is a vertical cross section view of an embodiment of an ultrasonic dental attachment, with an embedded RFID reader, placed over teeth with an embodiment of a clear aligner that has an embedded RFID transponder.
FIG. 11B is a vertical cross section view of the ultrasonic dental attachment of FIG. 11A, when not placed over teeth, with an embedded RFID reader.
Figure 12:
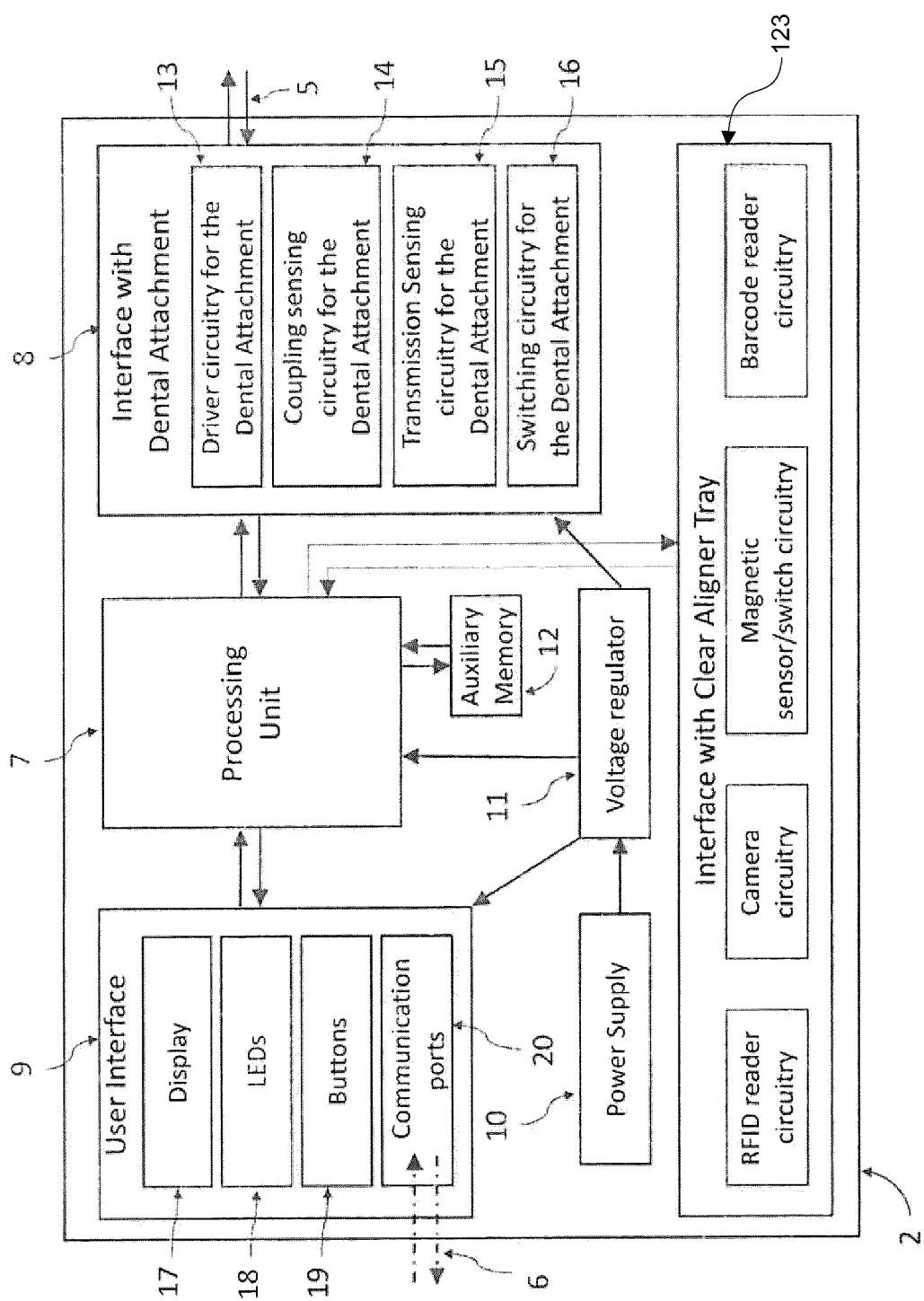
FIG. 12 is a block diagram of an embodiment of an external electronics controller with an interface with a clear aligner tray (e.g., RFID reader circuitry, camera circuitry, magnetic sensor/switch circuitry, or barcode reader circuitry)

In one example, radio-frequency identification (RFID) could be used. RFID can use electromagnetic fields to automatically identify tags/transponders attached to objects. Two-way radio transmitter-receivers (writers/readers) can send a signal to the transponder and read its response. As shown in FIG. 10, an RFID transponder 111 that can include the treatment information for a specific tray can be placed on/in that clear aligner tray 58. Note in some embodiments, the RFID transponder can be located at the tooth crown level while the treatment can be delivered at the tooth root level so that there is no interference with the ultrasound treatment. The RFID transponder (e.g., Murata LXMS33HCNG-134, Texas Instruments RF37S114) can be embedded into or affixed onto (e.g., with epoxy) the clear aligner tray. With an RFID transponder 111 on each clear aligner tray 58, the ultrasound device can use an RFID reader 112 to read the treatment information. The RFID reader circuitry, comprising a writer/reader integrated circuit (e.g., Texas Instruments TRF7960/TRF7961) and an antenna, can be placed in the mouthpiece 3, or the handheld electronics 2, or a combination of the two. In any case, the clear aligner tray's RFID transponder can be read by ultrasound device 1 when the patient brings the clear aligner tray 58 within a desired proximity of ultrasound device 1. The ultrasound device 1 can then interpret the treatment information and enable the desired ultrasound treatment zones for that specific clear aligner tray. FIGS. 11A and 11B shows an example of the RFID reader 112 in the ultrasonic dental attachment 3, while FIG. 12 shows how the RFID reader 112 could be incorporated into the handheld electronics 2. As shown in FIG. 12, communication module circuitry 123 can communicate with processing unit 7 and communication module circuitry 123 can be configured to come in a form specific to the type of communication module being used (for example, any one of, or combination of: RFID, camera, magnetic, barcode, or other).

Figure 13:
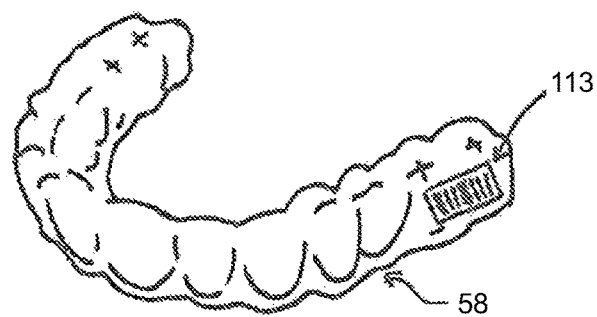
FIG. 13 is a perspective view of an embodiment of a clear aligner tray with an embodiment of a scannable code.
Figure 15:
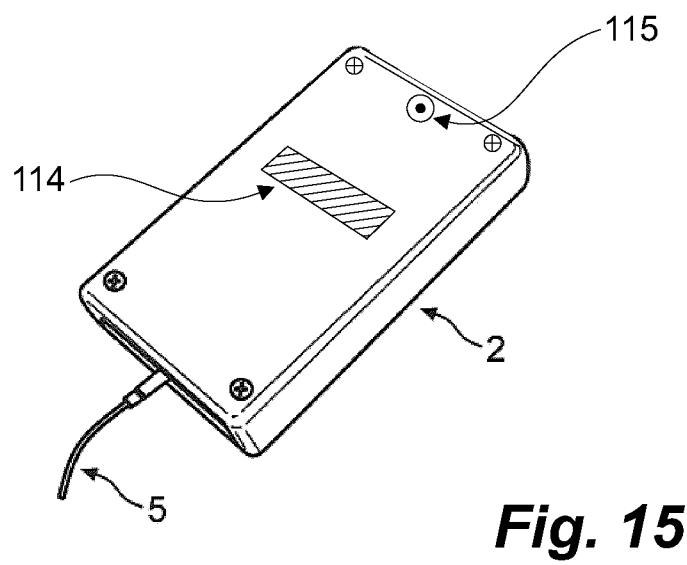
FIG. 15 is a perspective view of an embodiment of an external electronics controller with an embodiment of a camera and a barcode reader.

In another example, a scannable code 113, such as a bar code, that can include the treatment information for a specific tray can be placed on the clear aligner tray 58 by the tray manufacturer or a third party. The code 113 can be printed directly onto the clear aligner tray or attached onto its surface. A scannable code can be an optical, machine-readable, representation of data, or link to data, which can describe something about the object that carries the code. In this case, the barcode on a tray 58 can include information such as which teeth 22 are being moved by that specific tray 58. Code types that could be attached to or printed on the clear aligner trays include linear barcodes (e.g. Universal Product Code (UPC) barcode) or matrix barcodes (e.g. QR code). FIG. 13 shows an example of a clear aligner tray 58 with scannable code, such as a barcode, 113 on it. In this example, the handheld electronics 2 can require an optical method of reading the barcode, such as a barcode reader 114 or applications software using a camera 115. The patient would scan the clear aligner tray's barcode with the handheld electronics 2 and the ultrasound device can then interpret the treatment information and enable the desired ultrasound treatment zones for that specific clear aligner tray. FIGS. 12, 13, and 15 show an example of how a code reader 114 or a camera 115 could be incorporated into the handheld electronics 2. In FIG. 15, the battery cover is not shown on the handheld electronics 2, but handheld electronics 2 could have an internal battery.

Figure 16:
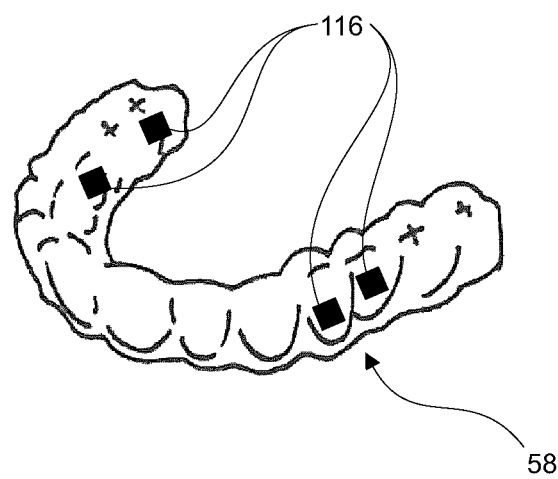
FIG. 16 is a perspective view of an embodiment of an embodiment of a clear aligner tray with embedded magnetic material.

In yet another example, the material properties of the aligner trays 58 could be modified (e.g., embedding another material during production) at the physical location of each tooth that is to be moved. The simple presence of the material or a property of the material could be detected by either the mouthpiece 3 or the handheld electronics 2. The ultrasound device 1 can then interpret the information and enable the desired ultrasound treatment zones for that specific aligner tray. As an example of material properties being used, magnetic material 116 could be embedded into the aligner trays in the physical location of each tooth that is being moved. FIG. 16 shows an example of the magnetic material 116 embedded in the aligner tray 58. Either the presence of the magnetic material 116 or the polarity of the magnetic material 116 could be used to communicate the desired ultrasound treatment zones. The mouthpiece 3 or the handheld electronics 2 would then read this information and enable the desired ultrasound treatment zones for that specific clear aligner tray. For the case when the ultrasonic dental attachment 3 reads this information when in proximity with the clear aligner, the ultrasonic dental attachment 3 can have incorporated in its structure an array of magnetic sensors or switches (e.g., Coto Technology™ Redrock® RR130 TMR) 118 that can detect the presence/absence of the magnetic material and/or its polarity. The magnetic sensors 118 can be connected through the ultrasonic dental attachment 3 cable 5 to the handheld electronics 2 and the information from the sensors 118 can then be interpreted by the microcontroller 7 of the handled electronics 2 to enable the desired ultrasound treatment zone for that specific tray. FIGS. 17A and 17B show the magnetic sensor 118 incorporated into the ultrasonic dental attachment 3. For the case when the handheld electronics 2 reads this information when in proximity to the clear aligner 58, the handheld electronics 2 can have incorporated on one of its flat surfaces an array of magnetic sensors or switches 118 with a similar shape to the array of magnets 116 in the tray 58. When the tray is placed in proximity to the magnetic sensor 118 array, the information from the tray can be read by the sensors 118 and interpreted by the microcontroller 7 of the handheld electronics 2 to enable the desired ultrasound treatment zone for that specific tray 58. FIGS. 12 and 18 show how circuitry for the magnetic sensors/switches 118 could be incorporated into the handheld electronics 2.

In another example of material properties being used, an optical property of the clear aligner at the physical location of each tooth to be moved could be used. These optical properties could include adding colored dots 119 or adjusting the light interaction properties 120 (e.g., reflectivity, transmissivity, polarization) of the clear aligner in the physical location of each tooth to be moved. The ultrasonic dental attachment 3 or the handheld electronics 2 could then read this information and enable the desired ultrasound treatment zones for that specific clear aligner tray.

Figures 14A, 14B:
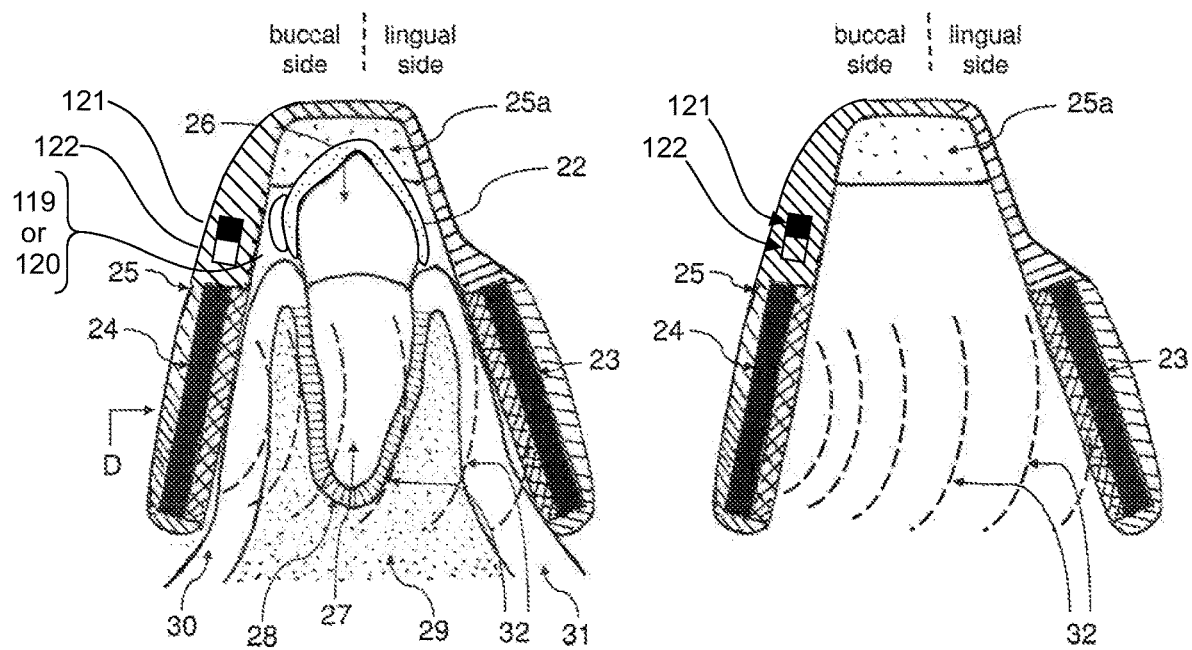
FIG. 14A is a vertical cross section view of an embodiment of an ultrasonic dental attachment, with an embodiment of an embedded light emitter and light sensor, placed over teeth with an embodiment of a clear aligner that has embedded colored dots or light interaction properties.
FIG. 14B is a vertical cross section view of the ultrasonic dental attachment of FIG. 14B, not placed over teeth, with an embedded light emitter and light sensor.
Figure 20:
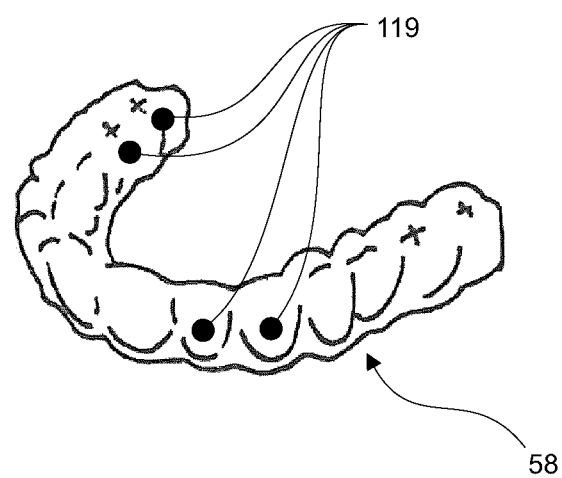
FIG. 20 is a perspective view of a clear aligner tray with an embodiment of colored dots.
Figure 21:
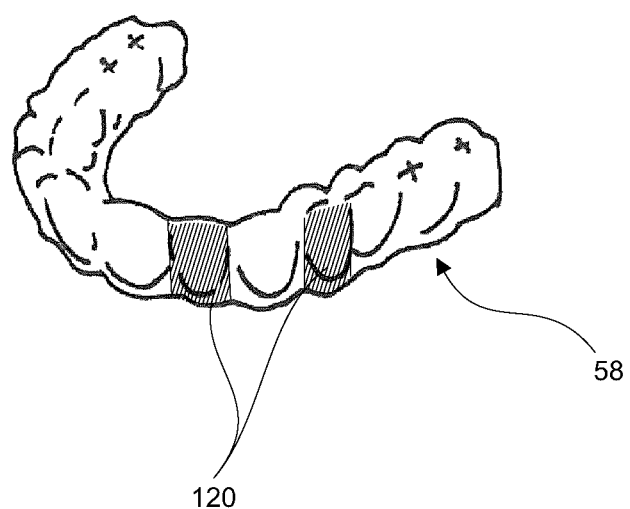
FIG. 21 is a perspective view of an embodiment of an embodiment of a clear aligner tray with an embodiment of a selectively changed surface.

FIG. 20 shows an example of the clear aligner tray 2 with colored dots 119. FIG. 21 shows an example of the clear aligner tray 2 with the surface reflectivity of aligner 58 selectively changed. If ultrasonic dental attachment 3 is used to read this information when in proximity with the clear aligner 58, ultrasonic dental attachment 3 can have incorporated in its structure an array of photodiodes (light sensors) 121 and light emitting diodes (light emitters) 122 (e.g., Sharp™ GP2S60). The light sensors would detect a different reflected light coming from the tray 58 (e.g., depending on the surface reflectivity or color) thus reading the information of tray 58 regarding what ultrasound zone is to be activated. FIGS. 14A and 14B show ultrasonic dental attachment 3 with an embedded light sensor 121 and light emitter 122 to detect the colored dots 119 and/or light interaction properties 120. The light sensors 121 can be connected through ultrasonic dental attachment 3 cable 5 to the handheld electronics 2 where the microcontroller 7 can receive the information from the light sensors 121 and can enable the desired ultrasound treatment zone for that specific tray 58. If the handheld electronics 2 is used to read this information, this can be done using a camera 115 incorporated in the handheld electronics 2 and/or applications software that can recognize the optical features of the tray 58 (e.g., colored dots, reflectivity), and then the microcontroller 7 of the handheld electronics 2 can activate the desired ultrasound treatment zones for the specific tray 58. FIG. 2 shows an example of how circuitry for camera 115 could be incorporated into the handheld electronics 2.

The embodiments mentioned herein can not only allow an ultrasound device to activate the treatment zones where tooth movement is desired for each tray, but can also allow the ultrasound device to detect the presence or absence of the clear aligner tray. For example, this feature can be used to automatically turn on ultrasound treatment when ultrasonic dental attachment 3 detects the presence of the clear aligner 58, or to not turn on the ultrasound treatment if no aligner 58 is detected. A similar detection feature can be used by having an RFID attached to the orthodontic bracket (in the case of wire braces) and the device can activate only when it detects the RFID, which means that it will activate only when ultrasonic dental attachment 3 is in the mouth, and/or proximate the bracket. This feature can also be used to automatically turn on or off the ultrasound treatment when ultrasonic dental attachment 3 is in the mouth or is removed from the mouth.

Use of the systems, methods, and apparatuses described herein can also result in better tracking of the clear aligners ("tracking" is when teeth are moving as planned in the treatment setup), as an ultrasound device can accelerate bone remodeling and can allow more difficult and slow types of tooth movement (which are normally more unpredictable) to happen at a faster rate and, therefore, more probable completion of the tooth movement within the time of a tray usage interval. With the teeth being moved to their desired locations with a higher probability, the treatment end result can have a higher probability to be as initially planned. Also, it will be less probable that mid-treatment corrections will be required, which normally results in the manufacture of new trays to be required. This can be advantageous not only for the tray manufacturer (since fewer trays will be manufactured) but also for the orthodontist (since it will reduce the number of patient visits) and the patient (since it will reduce treatment time by eliminating the time required to wait for mid-treatment corrections).

Although a few embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

While the above description details certain embodiments of the invention and describes certain embodiments, no matter how detailed the above appears in text, the invention can be practiced in many ways. Details of the apparatuses and methods may vary considerably in their implementation details, while still being encompassed by the invention disclosed herein. These and other changes can be made to the invention in light of the above description.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification. Accordingly, the actual scope of the invention encompasses not only the disclosed embodiments, but also all equivalent ways of practicing or implementing the invention.

The above description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. The elements and acts of the various embodiments described above can be combined to provide further embodiments.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

We claim:

1. A system comprising:
   an orthodontic appliance selected from orthodontic aligners and wire braces, the orthodontic appliance comprising:
   a body configured to move at least one tooth; and
   an information component in or on the body, wherein the information component comprises a location of at least one tooth where orthodontic tooth movement is desired or a location of one or more teeth for which orthodontic tooth movement is not desired;
   an intra-oral ultrasonic dental attachment comprising:
   a reader component that reads the information component in or on the orthodontic appliance;
   at least one flexible array of cooperative ultrasound transducers for emitting ultrasound, and
   a processing unit in communication with the reader component and the at least one flexible array of cooperative ultrasound transducers to selectively activate the at least one flexible array of cooperative ultrasound transducers to emit ultrasound to only the at least one tooth where orthodontic tooth movement is desired and not the one or more teeth for which orthodontic tooth movement is not desired, in response to the reader component reading the information component; and
   wherein the reader component of the intra-oral ultrasonic dental attachment and the information component of the orthodontic appliance are each positioned at tooth crown level such that the reader component and the information component are adjacent when the intra-oral ultrasonic dental attachment and the orthodontic appliance are positioned in a patient's mouth,
   wherein the reader component automatically reads the information component when the intra-oral ultrasonic dental attachment and the orthodontic appliance are positioned in the patient's mouth; and wherein the reader component reads the information component at the tooth crown level while the at least one flexible array of cooperative ultrasound transducers emits the ultrasound at tooth root level.

2. The system of claim 1 wherein the information component is in the form of at least one of: a radio-frequency identification (RFID) transponder, a scannable code, a change in material properties, and a change in optical properties.

3. The system of claim 2 wherein the information component is in the form of the change in material properties, and wherein the change in material properties is provided by embedded magnetic material.

4. The system of claim 2, wherein the information component is in the form of the change in optical properties, and wherein the change in optical properties is provided by at least one of colored dots and light interaction properties.

5. The system of claim 2, wherein the information component is in the form of the scannable code, and wherein the scannable code comprises a linear barcode or a matrix barcode.

6. The system of claim 1, further comprising an external controlling means for controlling the ultrasound, the external controlling means being in communication with the intra-oral ultrasonic dental attachment.

7. A communication module for providing multiplicative treatment-duration shortening for a patient under orthodontic treatment, the communication module comprising:
- a reader component contained within an intra-oral ultrasonic dental attachment, the intra-oral ultrasonic dental attachment comprising at least one flexible array of ultrasonic transducers;
- an information component in or on an orthodontic appliance for conducting orthodontic treatment, wherein the information component is readable by the reader and includes one or more operational parameters of the intra-oral ultrasonic dental attachment;
- wherein the reader component of the intra-oral ultrasonic dental attachment and the information component of the orthodontic appliance are each positioned at tooth crown level such that the reader component and the information component are adjacent when the intra-oral ultrasonic dental attachment and the orthodontic appliance are positioned in the patient's mouth;
- wherein the reader component automatically reads the information component when the intra-oral ultrasonic dental attachment and the orthodontic appliance are positioned in the patient's mouth;
- wherein the one or more operational parameters comprise a location of at least one tooth where the orthodontic tooth movement is desired or a location of one or more teeth for which orthodontic tooth movement is not desired;
- wherein the at least one flexible array of ultrasonic transducers is activatable, in response to the reader component reading the information component, to selectively emit ultrasound to only the at least one tooth where orthodontic tooth movement is desired and not the one or more teeth for which orthodontic tooth movement is not desired.

8. The communication module of claim 7, wherein the reader component comprises a radio-frequency identification (RFID) reader and the information component is in the form of an RFID transponder.

9. The communication module of claim 7, wherein the reader component comprises a barcode reader and the information component is in the form of a scannable code.

10. The communication module of claim 9, wherein the barcode reader is a linear barcode reader and the scannable code is a linear barcode.

11. The communication module of claim 9, wherein the barcode reader is a matrix barcode reader and the scannable code is a matrix barcode.

12. The communication module of claim 9, wherein the barcode reader comprises a camera.

13. The communication module of claim 7, wherein the reader component comprises at least one sensor or switch for reading material properties and the information component is in the form of a change in material properties.

14. The communication module of claim 13, wherein the at least one sensor or switch comprises an array of magnetic sensors or switches and wherein the change in material properties is provided by embedded magnetic material.

15. The communication module of claim 7, wherein the reader component comprises at least one sensor for reading optical properties and wherein the information component is in the form of a change in optical properties.

16. The communication module of claim 15, wherein the reader component further comprises at least one light emitter.

17. The communication module of claim 16, wherein the at least one sensor comprises an array of photodiodes and the at least one light emitter comprises light emitting diodes.

18. The communication module of claim 17, wherein the change in optical properties is provided by at least one of colored dots and light interaction properties.

19. The communication module of claim 7, further comprising an external controlling means in communication with the intra-oral ultrasonic dental attachment to selectively activate the at least one flexible array of ultrasonic transducers pursuant to the one or more operational parameters.

* * * * *